United States Patent [19]

Spencer

[11] 4,417,935
[45] Nov. 29, 1983

[54] METHOD OF DIAPER MANUFACTURE

[75] Inventor: Harvey J. Spencer, Green Bay, Wis.

[73] Assignee: Paper Converting Machine Company, Green Bay, Wis.

[21] Appl. No.: 310,881

[22] Filed: Oct. 13, 1981

[51] Int. Cl.$^3$ .................. B32B 31/08; B32B 31/10
[52] U.S. Cl. ........................................ 156/80; 2/401;
2/402; 156/164; 156/229; 156/269; 156/291;
156/301; 156/324; 156/498; 604/358; 604/372;
604/385; 604/400
[58] Field of Search .................. 128/284, 287, 290 P,
128/290 R; 156/80, 164, 229, 291, 244.11, 324,
498, 269, 301; 2/237, 401, 402; 427/208.2,
398.2; 604/358, 372, 385, 400

[56] References Cited

U.S. PATENT DOCUMENTS

| | | | |
|---|---|---|---|
| 3,578,155 | 5/1971 | Small et al. | 128/287 X |
| 3,599,293 | 8/1971 | Nystrand et al. | 241/146 X |
| 3,860,003 | 1/1975 | Buell | 128/287 |
| 3,943,605 | 3/1976 | Nystrand | 156/62.8 X |
| 4,022,456 | 5/1977 | Hooper et al. | 270/65 |
| 4,050,462 | 9/1977 | Woon et al. | 128/287 |
| 4,059,714 | 11/1977 | Scholl et al. | 156/78 X |
| 4,076,570 | 2/1978 | Medley et al. | 156/244.11 |
| 4,081,301 | 3/1978 | Buell | 156/164 |
| 4,156,754 | 5/1979 | Cobbs et al. | 156/78 X |
| 4,227,952 | 10/1980 | Sabee | 156/164 |
| 4,239,578 | 12/1980 | Gore | 156/361 |
| 4,261,782 | 4/1981 | Teed | 156/361 |
| 4,284,454 | 8/1981 | Joa | 156/163 |
| 4,293,367 | 10/1981 | Klasek et al. | 156/494 |
| 4,297,157 | 10/1981 | Van Vliet | 156/164 |
| 4,300,967 | 11/1981 | Sigl | 156/164 |
| 4,333,782 | 6/1982 | Pieniak | 156/164 |

*Primary Examiner*—Robert A. Dawson
*Attorney, Agent, or Firm*—Tilton, Fallon, Lungmus & Chestnut

[57] ABSTRACT

A method of diaper manufacture whereby adhesive is applied directly to the moisture impervious web for attachment thereto of elastic ribbons to make a shirred diaper.

2 Claims, 2 Drawing Figures

METHOD OF DIAPER MANUFACTURE

BACKGROUND AND SUMMARY OF INVENTION

This invention relates to a method of diaper manufacture and, more particularly, to a method of making "elasticized" diapers.

A method of making elasticized diapers is seen in U.S. Pat. No. 4,081,301 wherein elastic ribbons are stretched, i.e., placed under tension, adhesive applied thereto, and thereafter the adhesive-equipped, tensioned elastic ribbons are applied to a moisture impervious web. This web is then integrated with the remainder of the diaper and the continuous webs making up the diaper portion transversely cut, folded and packaged for shipment. All of this is done automatically and in continuous fashion so as to reduce the cost of the disposable diapers.

A significant drawback has attended this operation because of the application of adhesive to the elastic ribbons. The ribbons being relatively thin, have a tendency to twist which could result in imperfect attachment of the ribbons to the diaper. When this occurs, the diaper is faulty because the desired stretching for fit around the baby's leg is not achieved. Therefore, the art workers have gone to the extraordinary expedient of applying adhesive to both sides of the elastic ribbon in the hope that this would avoid the just mentioned drawback. However, this has not been successful and, as a result, the machines manufcturing diapers have to be shut down from time-to-time in order to untwist the ribbons, thereby reducing production and increasing waste causing higher cost to the consumer.

Through the provision of a novel adhesive application procedure, the instant invention avoids the problems and drawbacks of the just described diaper machine operation. More particularly, the invention makes use of an adhesive which is applied directly to the impervious web so that there is no treatment required on the elastic ribbons and twisting thereof becomes inconsequential.

Other objects and advantages of the invention may be seen in the ensuing portion of the specification.

The invention is described in conjunction with the accompanying drawing, in which FIG. 1 is a schematic flow diagram of the operation of the diaper making machine; and FIG. 2 is a side elevational view, essentially schematic of the portion of the diaper machine with which the instant invention is concerned.

DETAILED DESCRIPTION

Figure 1:
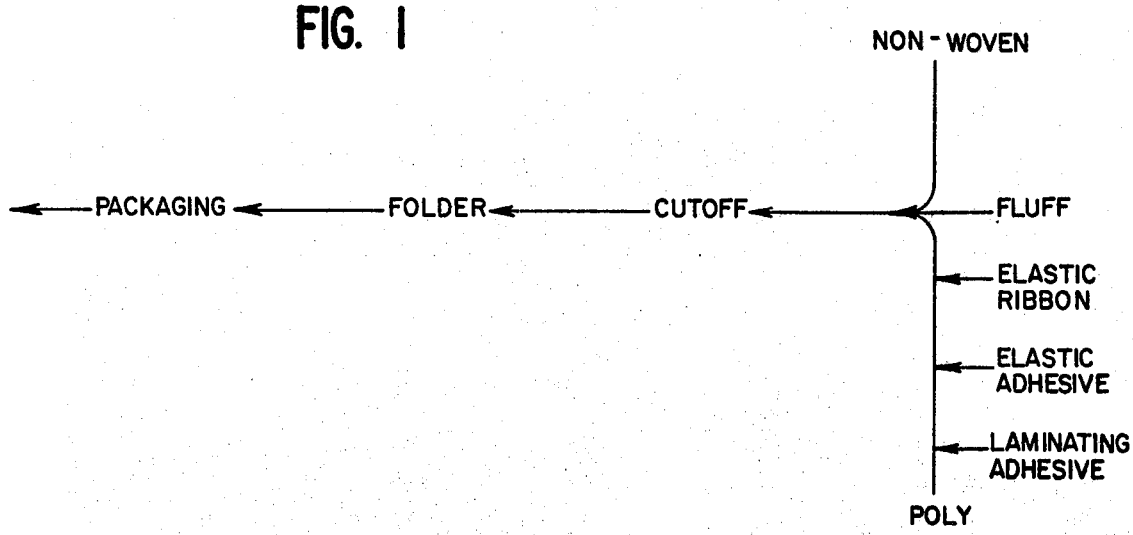

In the illustration given and with reference first to FIG. 1, a typical flow diagram illustrates the components and procedural steps employed in the manufacture of disposable diapers. At the extreme right of FIG. 1, it is seen that adhesive is applied to the poly and the tensioned elastic is added prior to integration of the POLY-FLUFF-NON-WOVEN combination. FLUFF becomes the absorbent pad portion of the diaper. the NON-WOVEN is the surface of the diaper positioned next to the infant and is moisture pervious whereas the so-called poly or moisture impervious web (normally constructed of polyethylene) is positioned outwardly. The integrated materials are then directed to a cutoff station, then to a folder and finally to packaging so that starting with the several raw materials, a machine can produce packages of 12, 24, etc. diapers at relatively high speed—of the order of 250 or more diapers per minute.

Figure 2:
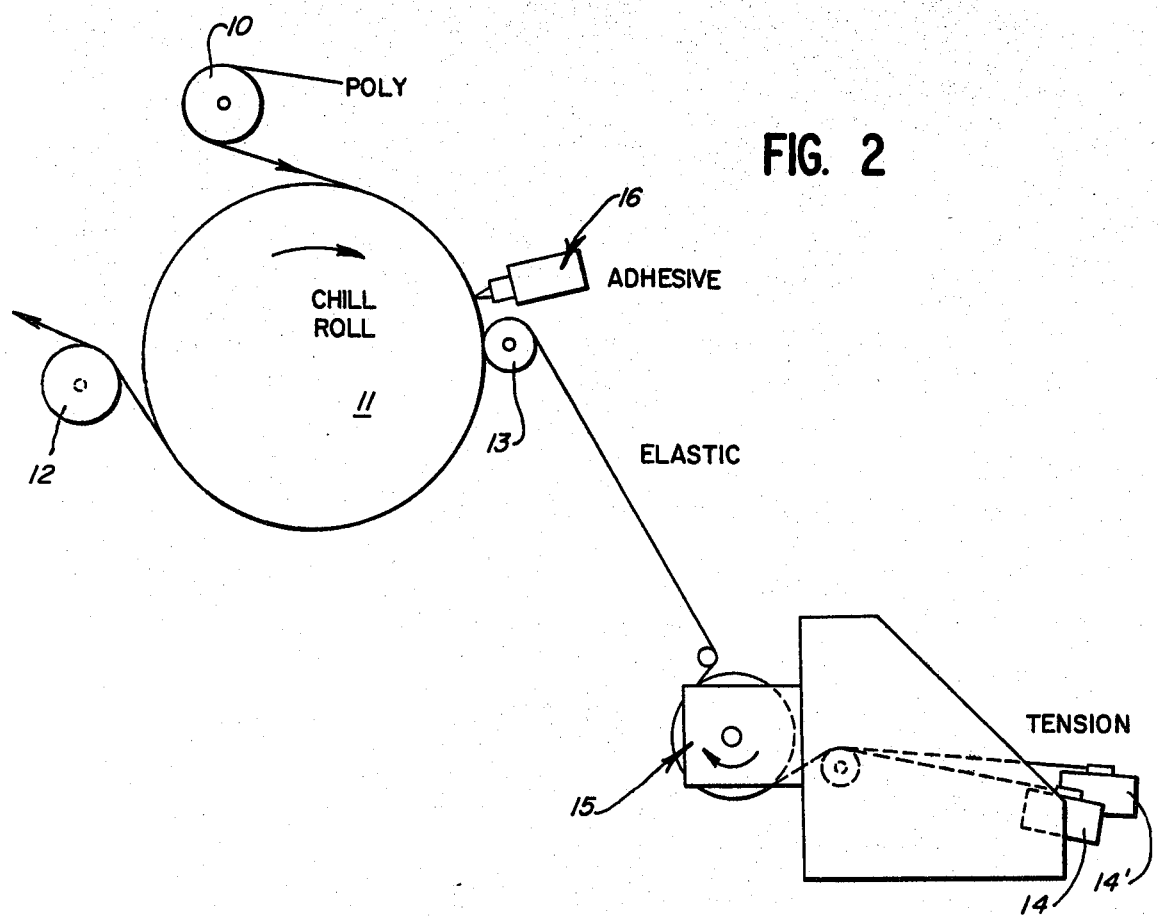

Referring now to FIG. 2, the portion of the diaper making machine employed for uniting the moisture impervious web with the elastic ribbon is shown. A wide variety of elasticized ribbons may be used, depending upon the choice of the diaper manufacturer. In the upper central portion, the moisture impervious web designated POLY is seen partially wrapped around a roll 10 suitably journalled within the side frames (not shown) of the machine. The poly web is then directed around a chill roll 11 also journalled in the frame and, after integration with the elastic ribbon, is directed around another roll 12 toward the station of union with the FLUFF and NON-WOVEN.

In the illustration given and still with reference to FIG. 2, the numeral 13 represents a roll around which the elastic ribbons (two provided in side-by-side relation) are wrapped. These elastic ribbons are the solid elastic ribbons normally used in the manufacture of elastic leg diapers. The elastic ribbons are derived from a box or reel source (not shown) which is generally located beside the machine for convenient reloading. The ribbons are passed through tension meters as at 14 and 14' (see the lower right hand portion of FIG. 2) which operate in conjunction with a pull roll arrangement to apply a predetermined tension to the ribbons. Prior to wrapping guide rolls 13 and chill roll 11, the elastic ribbon can pass over a heated roll 15 to preheat the ribbon for better adhesion to the poly web 10.

Adhesive is applied by means of a nozzle member generally designated 16 to the poly web shortly prior to the convergence of the elastic ribbons with the poly. Special adhesives with quick setting, low heat properties are necessary to avoid heat damage to the POLY. Found advantageous is an adhesive to be applied to the POLY such as polymeric synthetic rubber Type No. 295-336 available from Findley Adhesives, Inc. of Brookfield, Wisconsin and applied through a Model 1001A Nozzle Applicator available from Nordson Corporation of Amhurst, Ohio as seen in U.S. Pat. Nos. 4,059,714 and 4,156,754. The adhesive may be laid down in intermittent bands so as to limit the stretching of the diaper to a central longitudinal portion.

By virtue of using the heated, foamed adhesive, for example, a limited heat source is applied to the polyethylene web, thereby avoiding any burn or deformation which would otherwise damage the polyethylene web and cause an imperfect diaper. Because the foamed adhesive has a substatntial quantity of entrapped air and hence much lower mass, puncturing of the air bubbles (for example through a nip) still gives an adequate amount of adhesive for bonding the elastic ribbons and poly together but, because of the low mass and lower heat content, there is no burn through the very thin gauge polyethylene as would be the case with a conventional hot melt adhesive.

The poly is maintained against burn through and the like by means of a cooling roll such as the chill roll 11. More particularly, the polyethylene is of the order of 1½ mils thickness and is preserved from burn or puckering by virtue of the chill roll 11. The surface temperature of the chill roll is advantageously in the range of 45° to 50° F. to maintain the polyethylene below about 225° even when contacted by adhesive in the 325°-350° F. range. The polyethylene web 10 is advantageously wrapped over a substantial segment of the chill roll 11 before adhesive application.

The elastic ribbon normally has an untensioned width of about 1/4" and a thickness of 0.010". Under tension, this reduces to 3/16" width which satisfactorily overlaps a 1/16" bead of adhesive applied by the nozzle 16.

The invention provides a significant advantage, being the first time an adhesive is placed directly on the polyethylene to insure that regardless of how the elastic ribbon is twisted, a secure attachment to the polyethylene is obtained. This results in increased productivity of the machine by eliminating machine stoppage to untwist the elastic ribbon and thereby reduction of waste product. Application of adhesive to the POLY rather than the elastic has the advantage of better linear control of adhesive to the more stable POLY web. This results in less misregister of the POLY-adhesive-Elastic lamination and consequently, better product quality control, lower waste, less downtime for clean-up, and ultimately, a better low cost product. A further advantage accrues in the fact that the only operation performed on the elastic ribbon is the tensioning so that "draws" can be reduced and critical space occupancy minimized.

What is claimed is:

1. A method of attaching an elastic ribbon to a moisture impervious web comprising feeding an elastic ribbon to an assembly station in a uniformly stretched condition, feeding a moisture impervious web of substantially inelastic material to said assembly station, intermittently applying a foamed adhesive to said moisture impervious web just prior to said assembly station while said moisture impervious web is in contact with a cooling roll, adhering the stretched elastic ribbon to said moisture impervious web in the area occupied by said adhesive and immediately thereafter nipping said moisture impervious web and stretched elastic ribbon to puncture the air bubbles of the foam, integrating a second web and an absorbent pad means to said moisture impervious web, transversely severing the integrated webs and pad means, folding and packaging the diapers resulting therefrom.

2. A method of attaching an elastic ribbon to a moisture impervious web comprising feeding a solid elastic ribbon to an assembly station in a uniformly stretched condition, feeding a moisture impervious web of substantially inelastic material to said assembly station, intermittently applying a pair of longitudinally extending beads of adhesive having quick setting, low heat properties to said moisture impervious web just prior to said assembly station under conditions promotive of maintaining said moisture impervious web below puckering temperature while maintaining said adhesive with sufficient bonding strength to adhere said ribbon securely to said moisture impervious web when said ribbon and moisture impervious web are nipped together, adhering the stretched elastic ribbon to said moisture impervious web in the area occupied by said adhesive, integrating a second web and an absorbent pad means to said moisture impervious web, transversely severing the integrated webs and pad means, folding and packaging the diapers resulting therefrom.

* * * * *